United States Patent
Mitchell et al.

(10) Patent No.: US 11,579,329 B2
(45) Date of Patent: Feb. 14, 2023

(54) ESTIMATING WEAR FOR BHA COMPONENTS USING BOREHOLE HARDNESS

(71) Applicant: Halliburton Energy Services, Inc., Houston, TX (US)

(72) Inventors: Ian David Campbell Mitchell, The Woodlands, TX (US); Crystal M. Saadeh, Pearland, TX (US)

(73) Assignee: Halliburton Energy Services, Inc., Houston, TX (US)

(*) Notice: Subject to any disclaimer, the term of this patent is extended or adjusted under 35 U.S.C. 154(b) by 23 days.

(21) Appl. No.: 16/894,064

(22) Filed: Jun. 5, 2020

(65) Prior Publication Data
US 2020/0386905 A1 Dec. 10, 2020

Related U.S. Application Data

(60) Provisional application No. 62/858,282, filed on Jun. 6, 2019.

(51) Int. Cl.
*G01N 23/20* (2018.01)
*G01N 23/2055* (2018.01)
(Continued)

(52) U.S. Cl.
CPC ............... *G01V 5/12* (2013.01); *E21B 12/02* (2013.01); *E21B 49/005* (2013.01); *G01N 23/20* (2013.01);
(Continued)

(58) Field of Classification Search
CPC ............. G01N 23/20; G01N 23/20008; G01N 23/20066; G01N 23/20083;
(Continued)

(56) References Cited

U.S. PATENT DOCUMENTS

| 4,914,591 A | 4/1990 | Warren et al. |
| 6,353,799 B1 | 3/2002 | Nigel et al. |

(Continued)

FOREIGN PATENT DOCUMENTS

| CN | 108427657 B | * | 5/2021 | ........... G01N 23/207 |
| WO | 2015094221 A1 | | 6/2015 | |

OTHER PUBLICATIONS

English translation of CN108427657B by Patent Translate.*
GCC Application No. 2019/38663, First Examination Report, dated Feb. 20, 2021, 3 pages.

*Primary Examiner* — Allen C. Ho
(74) *Attorney, Agent, or Firm* — Delizio, Peacock, Lewin & Guerra

(57) ABSTRACT

Estimating wear on bottom hole assembly (BHA) components utilizes a rock hardness index using analysis of drill cutting. Estimating the amount of wear on borehole assembly components comprises measuring the rock properties in drilled cuttings from a borehole. A hardness value is assigned to each mineral present in the drilled cuttings. A hardness index is calculated for a drilled borehole interval. A wear resistance factor is assigned to each BHA component of the BHA. The wear resistance factor depends on the wear resistance of each BHA component. A wear value for each BHA component is calculated based on the hardness index for the drilled borehole interval, the wear resistance of the BHA component, and drilling parameters.

20 Claims, 8 Drawing Sheets

(51) Int. Cl.
*G01N 23/207* (2018.01)
*G01N 23/223* (2006.01)
*G01V 5/12* (2006.01)
*G01N 33/24* (2006.01)
*E21B 12/02* (2006.01)
*E21B 49/00* (2006.01)
*G01V 5/04* (2006.01)
*G01N 23/205* (2018.01)
*G01N 23/22* (2018.01)
*G01N 23/20091* (2018.01)

(52) U.S. Cl.
CPC ......... *G01N 23/205* (2013.01); *G01N 23/207* (2013.01); *G01N 23/2055* (2013.01); *G01N 23/2076* (2013.01); *G01N 23/20091* (2013.01); *G01N 23/22* (2013.01); *G01N 23/223* (2013.01); *G01N 33/24* (2013.01); *G01V 5/04* (2013.01); *G01N 2223/056* (2013.01); *G01N 2223/0566* (2013.01); *G01N 2223/076* (2013.01); *G01N 2223/616* (2013.01)

(58) Field of Classification Search
CPC ........... G01N 23/20091; G01N 23/201; G01N 23/203; G01N 23/205; G01N 23/2055; G01N 23/207; G01N 23/2076; G01N 23/22; G01N 23/2209; G01N 23/223; G01N 2223/056; G01N 2223/0566; G01N 2223/076; G01N 2223/616; G01V 5/04; G01V 5/045; G01V 5/06; G01V 5/08; G01V 5/085; G01V 5/12; G01V 5/125; G01V 5/14; G01V 5/145
USPC .......................................... 378/44–50, 70–90
See application file for complete search history.

(56) References Cited

U.S. PATENT DOCUMENTS

| | | | |
|---|---|---|---|
| 8,101,907 B2* | 1/2012 | Jacobi | G01V 5/101 |
| | | | 250/256 |
| 9,556,728 B2* | 1/2017 | de Reynal, Jr. | G01V 99/00 |
| 9,915,130 B2 | 3/2018 | Betsch et al. | |
| 10,920,496 B2* | 2/2021 | Anderle | E21B 10/43 |
| 2015/0198035 A1 | 7/2015 | De Reynal, Jr. | |

* cited by examiner

ESTIMATING WEAR FOR BHA COMPONENTS USING BOREHOLE HARDNESS

BACKGROUND

The disclosure generally relates to the field of data processing, and more particularly to error detection/correction and fault detection/recovery.

A bottom hole assembly (BHA) is the lower portion of a drill string which operates at the bottom of a wellbore to drill through a rock formation. BHAs consist of various components such as a bit surface, bit gauge protection, stabilizers, reamers, and other downhole components. The BHA provides a force for the bit to break the rock which corresponds to the rate of penetration of the bit. The force provided by the BHA and forces from contact with the borehole walls during drilling activity cause abrasive wear to the BHA components. The BHA is pulled out of the borehole when the bit is sufficiently worn, and a new bit is required, or if any other component of the BHA is defective or fails. Drilling time is affected by the rate of penetration and the number of times the BHA is retrieved from the wellbore.

BRIEF DESCRIPTION OF THE DRAWINGS

Embodiments of the disclosure may be better understood by referencing the accompanying drawings.

DESCRIPTION

The description that follows includes example systems, methods, techniques, and program flows that embody embodiments of the disclosure. However, it is understood that this disclosure may be practiced without these specific details. For instance, this disclosure refers to estimating the wear life remaining on BHA components during drilling in illustrative examples. Aspects of this disclosure can also be applied to design an appropriate BHA based on an estimated well prior to drilling. In other instances, well-known instruction instances, protocols, structures, and techniques have not been shown in detail in order not to obfuscate the description.

Overview

During drilling activity, abrasive wear of BHA components occurs due to contact with the borehole wall. Wear can cause one or more components to fail. When a component fails, the entire drill string, including the BHA, is pulled out of the borehole (POOH) and replaced. Waiting until a BHA component fails to perform a POOH operation can compromise wellbore design or the BHA components themselves. However, if the BHA is pulled out too early and the BHA still has more wear life remaining, valuable drilling time is lost. Thus, being able to estimate the wear on the BHA and each individual component allows the BHA to be removed from the wellbore before any component fails and compromises the wellbore design while maximizing drilling time.

Accordingly, a technique has been developed for accurately estimating the wear life remaining for a BHA by considering the rock properties and mineralogy of the rock formation being drilled along with the amount of wear exposure and force each BHA component is exposed to. The technique calculates a wear value for each BHA component and allows for determination of the appropriate POOH strategy. The wear value is calculated using an algorithm based on the hardness of the BHA component, a hardness index for a drilled borehole interval, and various drilling parameters. A hardness index for a rock type is calculated using a measured mineralogy of the rock. Known hardness properties associated with each mineral type can be associated with the minerals present in the measured mineralogy. The hardness index for the borehole interval is determined through an integration of the hardness index of the rock over the depth interval drilled (or to be drilled) by the BHA. The hardness index of the total rock is calculated by an algorithm incorporating the hardness index of the borehole interval.

The estimated wear value can be used as an estimator in real time or future operations. While drilling, the estimated remaining wear life can be used to flag when a BHA should be POOH. The estimated wear value may also be used to plan BHA strategy and design for a future well or to optimize the BHA design for a planned well to minimize wear. Using a wear value as an estimator for both real time and future operation planning reduces well drilling time.

Example Illustrations

Figure 1:
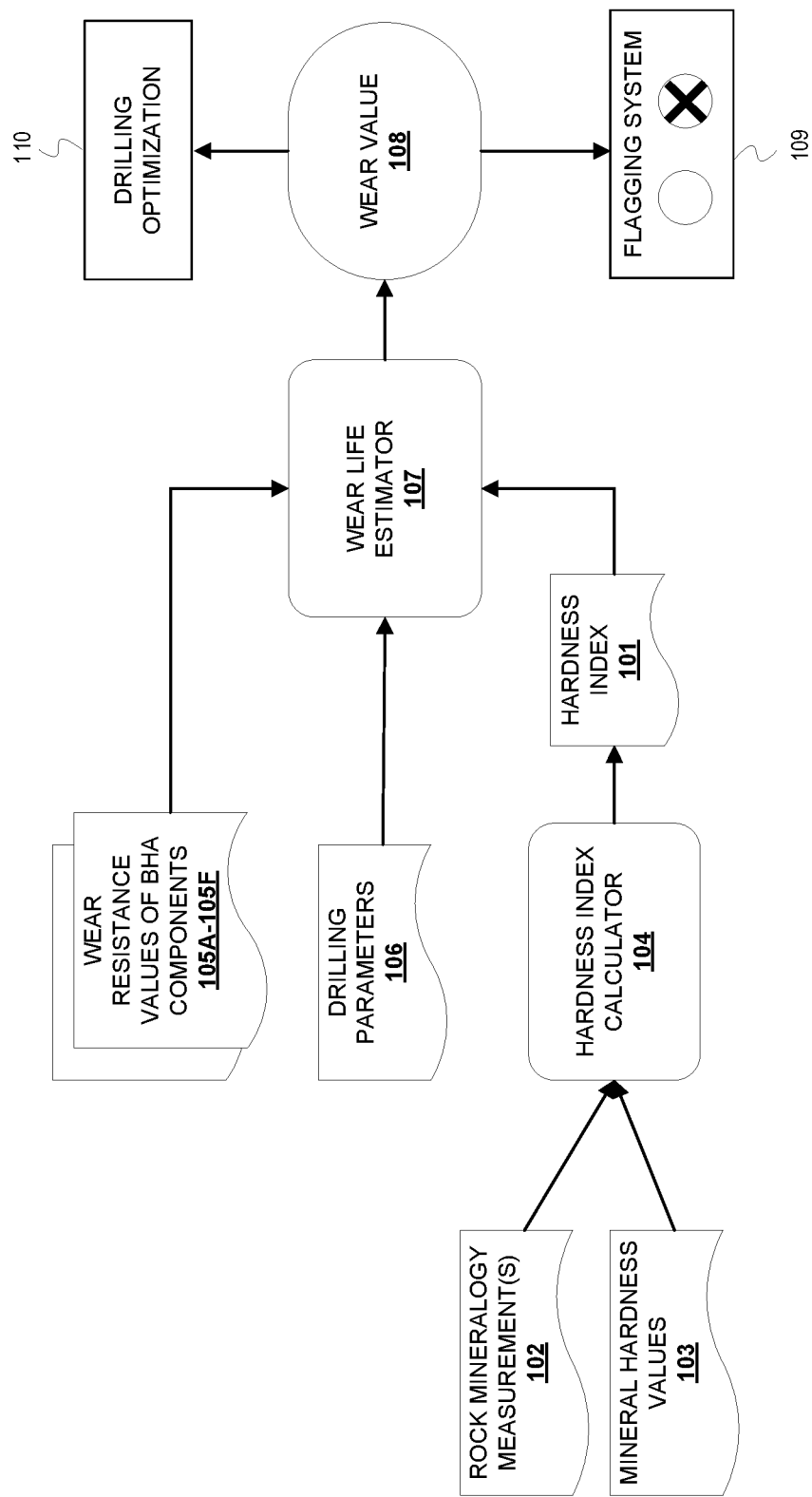
FIG. 1 depicts a schematic diagram of a process for estimating wear life on BHA components.

FIG. 1 depicts a schematic diagram of the process for estimating wear life on BHA components. The process for estimating wear life incorporates multiple types of data. Rock strength data is incorporated into the wear life through a hardness index 101. The hardness index 101 is determined using rock mineralogy measurements 102 and known values for mineral hardness 103. The rock mineralogy measurements 102 can include data obtained through x-ray fluorescence (XRF) and/or x-ray diffraction (XRD). XRF provides information relating to the elemental composition of the rock while XRD is a direct measurement of the physical properties, structure, and composition of the rock. This data can be obtained from cuttings of rock samples from the rock formation being drilled and/or data from the wellbore itself. The mineral hardness 103 is a rock property that is established by laboratory testing. A hardness index calculator 104 calculates the hardness index 101 using a hardness index algorithm.

Wear resistances 105A-105F of BHA components and drilling parameters 106 are also factors in the wear life. The wear resistances 105A-105F of BHA components represent the wear resistance of each BHA component. For example, wear resistance 105A may be the wear resistance of a bit gauge while wear resistance 105B may be the wear resistance of a stabilizer. While FIG. 1 depicts wear resistances 105A-105F of BHA components, some embodiments may have a different number of BHA components. The wear resistances 105A-105F of BHA components are determined by the properties of each BHA component. These properties can include material type, coatings, and outer protective measures of the BHA components, and BHA configuration. Drilling parameters 106 include forces acting on the BHA such as rotational forces, friction forces, and pressure forces resulting from contact with the borehole wall.

The hardness index 101, drilling parameters 106, and the wear resistances of BHA components 105A-F are used as input data for a wear life estimator 107. The wear life estimator 107 calculates a wear value 108 for each BHA component. The wear life estimator 107 may also utilize a stored history or database to learn and adapt to make estimates from offset wellbores. The wear value 108 is a numerical output of an estimated amount of wear on a BHA component or an estimated remaining life of a BHA component. The wear value 108 may be displayed on a user interface as a numerical value in terms of millimeters of wear on a material or as a percent wear value. The wear value 108 may also be displayed as a visual representation of the BHA in which the BHA components are shaded or colored according to the estimated wear value. For example, a BHA component with a low estimated wear value may appear green on the display, a BHA component approaching an estimated wear value satisfying a first (warning) threshold that corresponds to approaching possible compromise of drilling operation may be yellow, and a BHA component with an estimated wear value that satisfies a second (critical) threshold corresponding to high likelihood of pending compromise of drilling operations may be red.

The wear value 108 is used in a determination of POOH strategy during drilling and/or to optimize planning strategies for future drilling activity. A flagging system 109 can present an interface that provides the wear value itself and/or an indication of the expected wear on the BHA components based on the wear value 108. When the wear value 108 on the BHA components approaches a level that could compromise drilling operations, the flagging system 109 provides a flag indicating the BHA should be removed from the wellbore.

The wear value 108 can also be used for drilling optimization 110. Drilling optimization 110 can involve planning both the design of the BHA and the design of the wellbore. Drilling optimization 110 for planning the design of the BHA can include selecting the material hardness and bit design based on the wear value 108 for the material to fit the formation to be drilled. It can also include optimizing the BHA and BHA component design for a particular formation sequence. Drilling optimization 110 for planning the design of the wellbore can involve planning the trajectory of the wellbore to extend the wear life of the BHA components.

Figure 2:
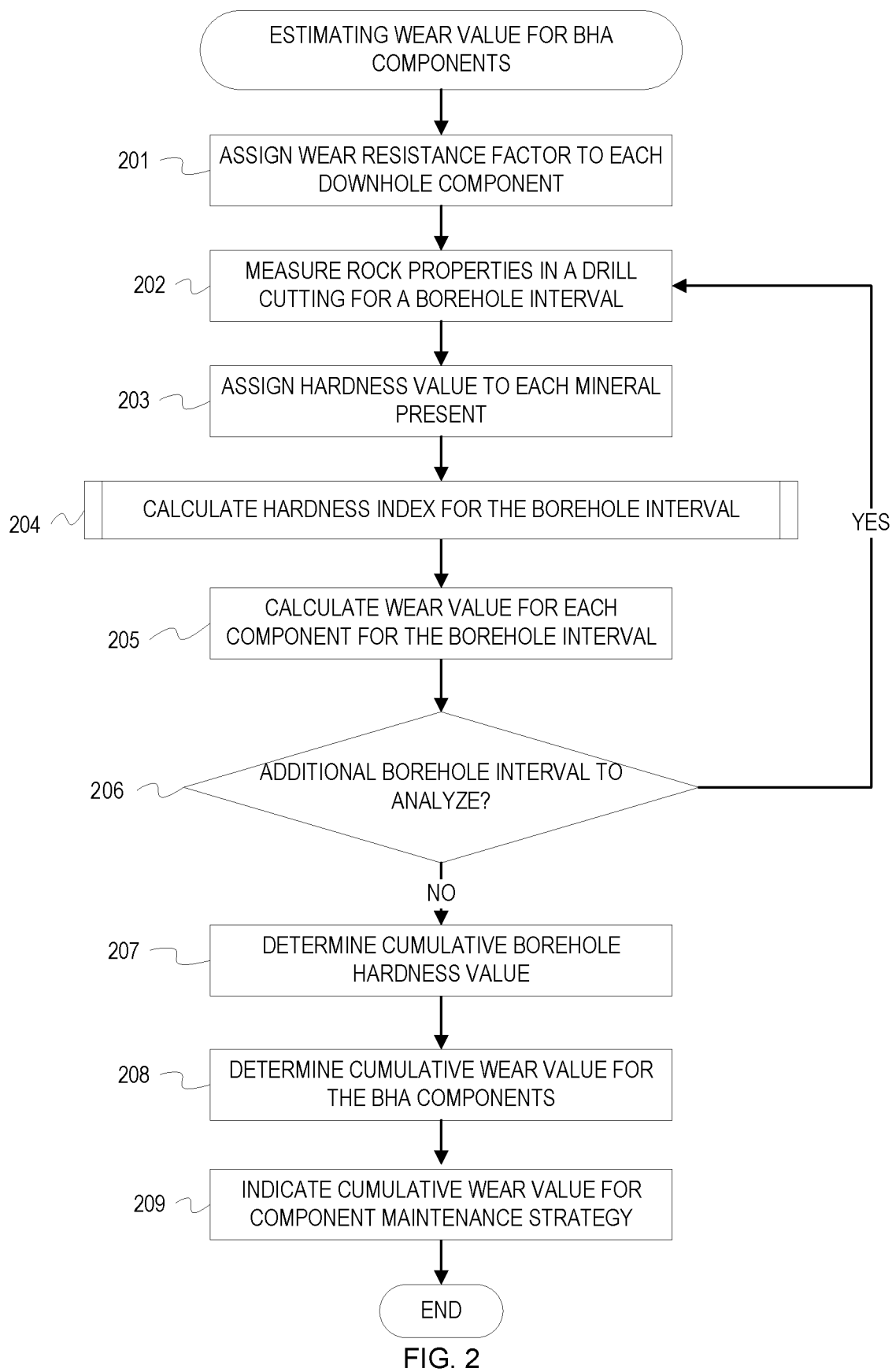
FIG. 2 depicts a flowchart of operations for estimating wear values for BHA components.

FIG. 2 is a flowchart of operations for estimating wear values for BHA components. FIG. 2 includes operations that can be performed by hardware, software, firmware, or a combination thereof. For example, at least some of the operations can be performed by a processor executing program code or instructions. Operations of the flowchart begin at block 201.

At block 201, a wear life estimator assigns a wear resistance factor to each downhole BHA component. The wear resistance factor of each component depends on the ability of the BHA component to resist wear during drilling activity. This factor can be affected by material type, protective coatings, and/or structural placement of the BHA component in the BHA.

At block 202, rock properties of a drill cutting are measured. Rock property measurements comprise measurements of the mineralogy of the drill cuttings such as the elemental composition of the drill cuttings and mineral type and concentration present in the drill cutting. Rock property measurements can be taken at the surface and/or downhole. Rock property measurements at the surface use XRF analysis to determine elemental composition of the rock. XRF determines the chemistry of a sample by measuring the fluorescent X-ray emitted from a sample when the sample is excited by a primary X-ray. XRF analysis can be performed in a lab on the drill cutting or on-site using a portable XRF device. Rock property measurements can be taken downhole using a downhole BHA component such as a wireline or logging while drilling (LWD) spectral gamma tool. Using rock property measurements obtained through both XRF and XRD methods provides a more complex representation of the rock by incorporating at least two different types of data and measurements from the wellbore itself and drill cuttings.

At block 203, the wear life estimator assigns a hardness value to each mineral detected from the sample analysis or downhole measurements. The hardness values may be known properties of minerals that can be looked up in a database of hardness values for minerals or the hardness values may be assigned based on the composition of the sample. For example, the hardness values may be based on the Mohs Hardness Scale in which the hardest mineral (diamond) is assigned a value of 10, and the lowest mineral (talc) is assigned a value of 1. Other minerals fall somewhere in between 1 and 10 based on a relative hardness. On the Mohs Hardness scale, calcite has a value of 3, and quartz has a value of 7. Other scales besides the Mohs hardness scale may also be used such as the Rosiwal Absolute Hardness Scale, the Vickers Scale, or any other scale or table of mineral hardness values.

In addition to or instead of a standardized scale, a relative and/or formation specific hardness scale can be used. The hardness value of each mineral may be assigned based on the composition of the borehole. The elemental composition determined in block 202 gives the types of minerals present in the borehole. From the list of mineral types, the minerals are assigned a hardness value relative to the other minerals present. The hardness value will be consistent with one of the previously described scales in terms of ranking of the mineral hardness, but the values will be adjusted to suit the specific mineral composition of the borehole. For example, the minerals quartz, calcite, and illite may all be present in a borehole sample. In this example, quartz has the greatest relative hardness of the minerals present, and illite has the least relative hardness with calcite falling in between. Because quartz has the greatest relative hardness of the minerals present, it is assigned the highest hardness value. Illite is assigned the lowest hardness value. For example, quartz may be assigned a value of 9, calcite may be assigned a value of 4, and illite may be assigned a value of 1. Adjusting the hardness value based on the minerals present allows for more accuracy when there is low variety in the samples by better showing the differences between similar mineral types often found in boreholes.

Figure 3:
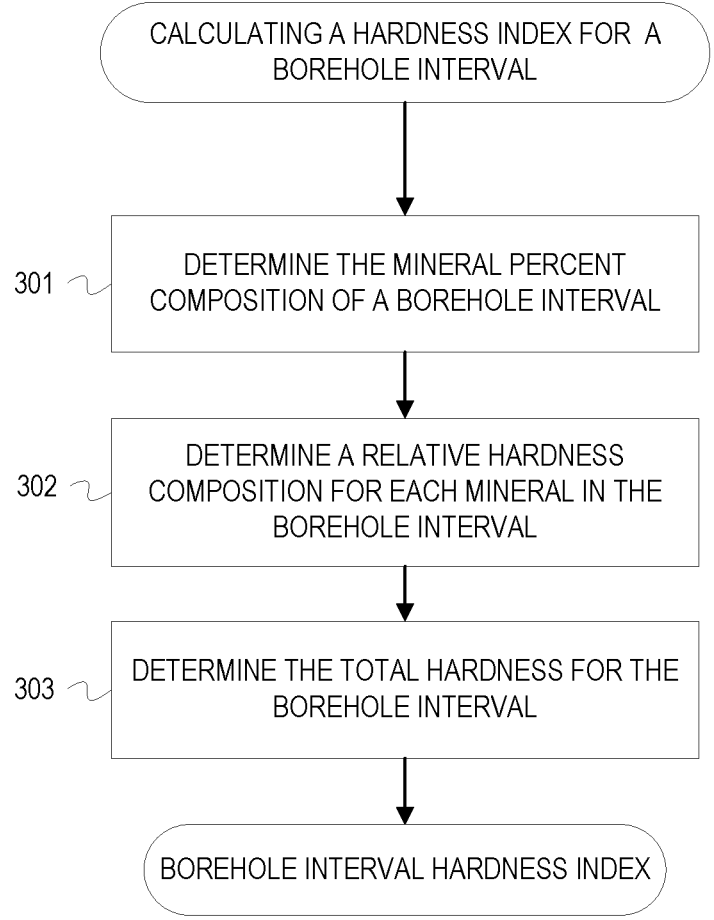
FIG. 3 depicts a flowchart of operations for calculating a hardness index for a borehole interval.

At block 204, a hardness index calculator calculates a hardness index for a drilled borehole interval. The hardness index calculator combines the hardness value assigned to each mineral in block 203 with the rock property measurements determined in block 202 to determine a rock hardness index for the drilled borehole interval. FIG. 3 describes operations for calculating a hardness index in greater detail.

At block 205, the wear life estimator calculates a wear value for each BHA component for the borehole interval. The wear value for each component is based on the total rock hardness index, the wear resistance factor of the component, and various drilling parameters. Drilling parameters such as rotation speed of the drill bit and well trajectory can affect the rate at which a BHA component wears down.

The wear value is a numerical value of an estimated amount of wear on a BHA component that can be used to estimate the remaining life of the component. The wear value is calculated based on the hardness of the BHA component, drilling parameters, and the total rock hardness index. The wear value can be a measurement of remaining material, such as a numerical value reported in millimeters of remaining material, a percent of material remaining, or an index number.

At block 206, the wear life estimator determines whether there is an additional borehole interval to analyze. If there is an additional borehole interval to analyze, then flow returns to block 202. Otherwise, operations continue to block 207.

At block 207, the wear life estimator determines a cumulative borehole hardness value. The cumulative borehole hardness value is the sum of the hardness indexes of each borehole interval, as determined in block 204. The hardness index for each borehole interval can be used to analyze instantaneous wear on the drill bit at a drilling depth.

At block 208, the wear life estimator determines the cumulative wear value for the BHA components. The cumulative hardness value can be used to analyze cumulative wear of each BHA component throughout the drilling process. The wear life estimator determines the cumulative wear value for each BHA component by summing the wear values for each borehole interval. The wear life estimator may also calculate the cumulative wear value for each BHA component directly from the cumulative hardness value. The cumulative hardness value and the cumulative wear value may represent any one or more borehole intervals. The cumulative values may also represent the entire drilled interval.

At block 209, a cumulative wear value is indicated for component maintenance strategy. The cumulative wear value can be presented via a user interface to inform a POOH strategy. An interface program can present the wear value itself, an alarm, a visual representation of the BHA, or drill string with annotation or visual emphasis (e.g., color coding) to indicate the extent of wear based on the wear value, etc. Indication of the wear value may be communicating the wear value to an alarm system or specified recipient. Based on the wear value, a decision can be made to continue drilling or to initiate removing the BHA from the wellbore. Assessing the POOH strategy with the wear value allows for a prediction of the optimum timing for removing the BHA from the wellbore.

In another embodiment, instead of individually calculating a hardness index and wear value for each borehole interval, a hardness index may be determined for multiple borehole intervals at once. The hardness index of each borehole interval may be maintained or stored in a database. The sum of the hardness indexes for each of the borehole intervals is maintained across the multiple intervals. The sum of the multiple borehole intervals, which may or may not be equal to the length of the drilled borehole, can then be used to calculate a single wear value for the multiple borehole intervals.

FIG. 3 depicts a flowchart of operations for calculating a hardness index for a borehole interval, as in block 203 of FIG. 2. The description refers to a program code that performs operations as a "hardness index calculator" although it is appreciated that program code naming and organization can be arbitrary, language dependent, and/or platform dependent. Operations of the flowchart of FIG. 3 begin at block 301.

At block 301, the mineral percent composition of a borehole interval is determined. A hardness index calculator defines a portion of the borehole as a borehole interval. The intervals may be defined based on distance or time. When a borehole interval is based on distance, the hardness index calculator may define a set distance or a set fraction of the total borehole. For example, the borehole interval may be defined to be a 10-meter interval, or a borehole interval may be defined to be 1/10 of the total length of the drilled or planned borehole. For a borehole interval based on time, the hardness index calculator may define a time to reset calculations. Alternatively, the borehole interval may be dynamically defined such that the frequency of calculations increases as cumulative wear on the BHA components is expected to increase. As the drilling time and the drilled distance increase, the BHA components experience greater cumulative wear. As such, early borehole intervals based on distance may be greater than later borehole intervals while early borehole intervals based on time may be less than later borehole intervals to account for the increased cumulative wear over time and distance drilled. The hardness index calculator obtains rock property measurements, such as the rock properties measured in block 202 of FIG. 2, for the defined borehole interval. The rock property measurements include the minerals present in the borehole interval as well as the concentration of minerals in terms of a percent.

At block 302, a relative hardness composition for each mineral in the borehole interval is determined. The hardness index calculator determines the relative hardness composition for each mineral in the borehole using the percent composition of the mineral in the borehole interval and a hardness value, such as the hardness value assigned in block 202 of FIG. 2. To determine the relative hardness composition, the percent composition of the mineral as a decimal is multiplied by the hardness value. The relative hardness composition (RHC) can be calculated using Equation 1:

$$RHC = (\text{Percent Compsition of Mineral}) * (\text{Hardness Value of the Mineral}) \quad \text{(Equation 1)}$$

For example, a borehole interval is composed of 80% illite, 15% calcite, and 5% quartz. Assuming the previous example hardness values (illite—1, calcite—4, quartz—9), the relative hardness index of illite would be 0.8, calcite would be 0.6, and quartz would be 0.45. The percent compositions and hardness values are provided for example only. Other minerals may be present and different hardness values may be used.

At block 303, a total hardness for the borehole interval is determined. The hardness index calculator sums the relative hardness compositions of each of the minerals in the borehole interval to obtain the total hardness for the borehole interval. For the example borehole of block 302, the total hardness for the borehole interval would be 1.85.

Figure 4:
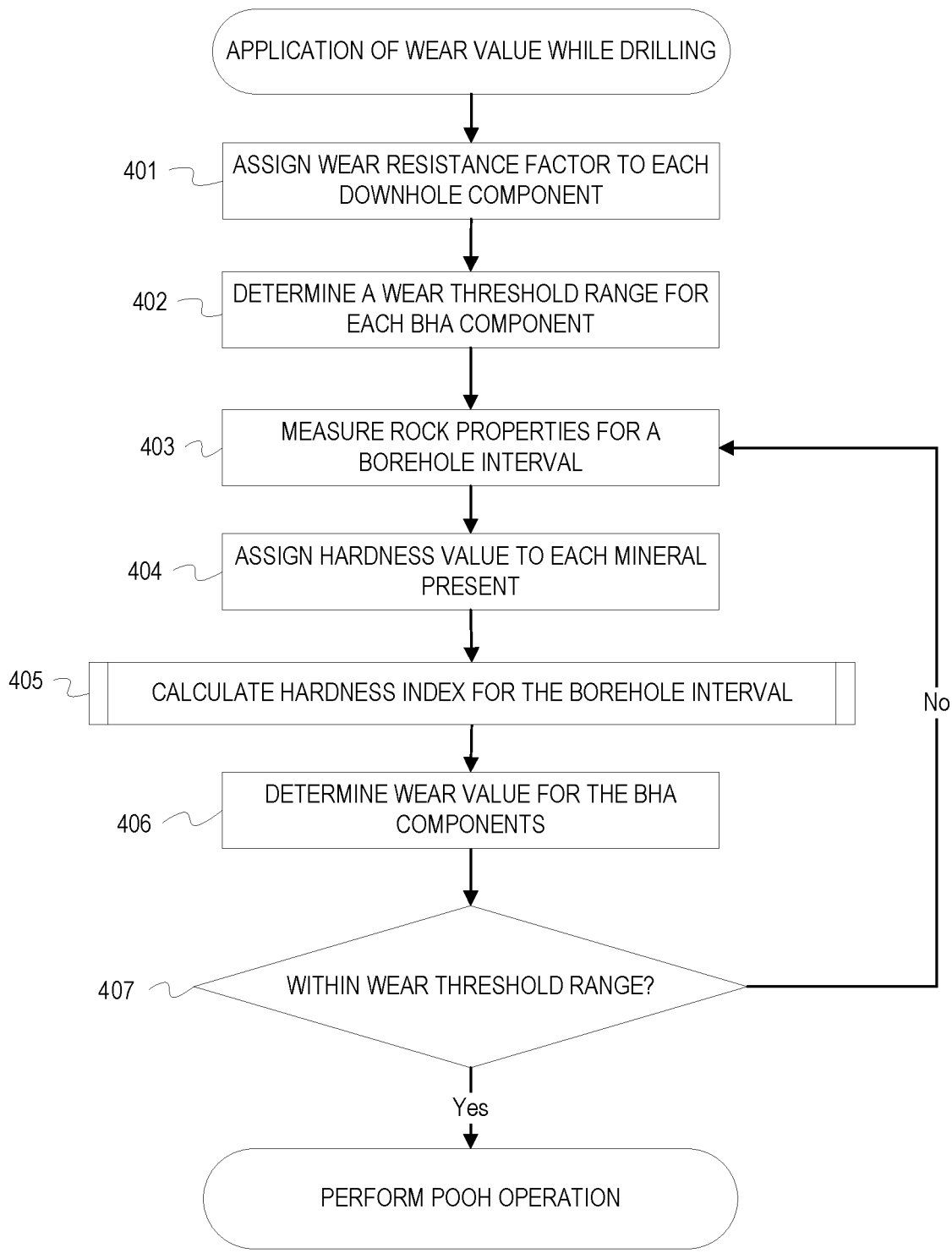
FIG. 4 depicts a flowchart of operations for an application of the wear value while drilling.
Figure 5:
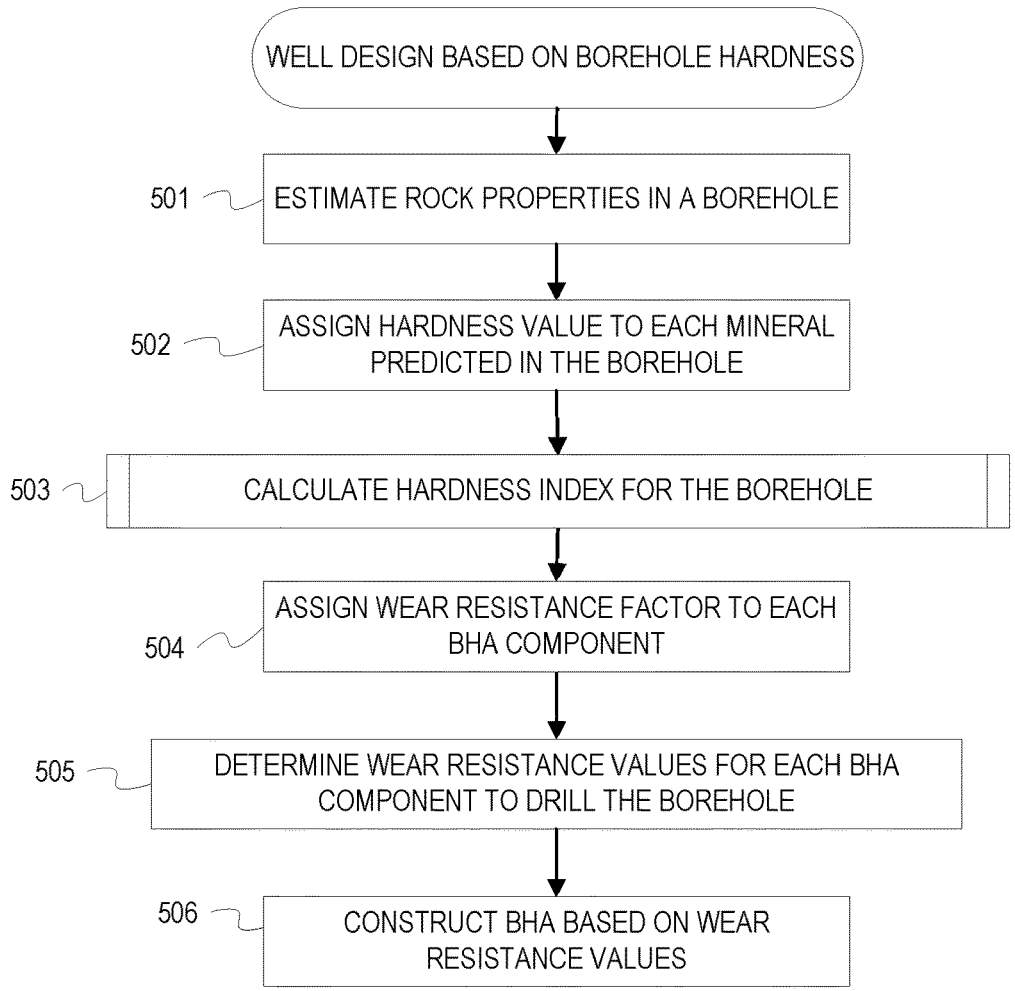
FIG. 5 depicts a flowchart of operations for designing a BHA based on borehole hardness.
Figure 6:
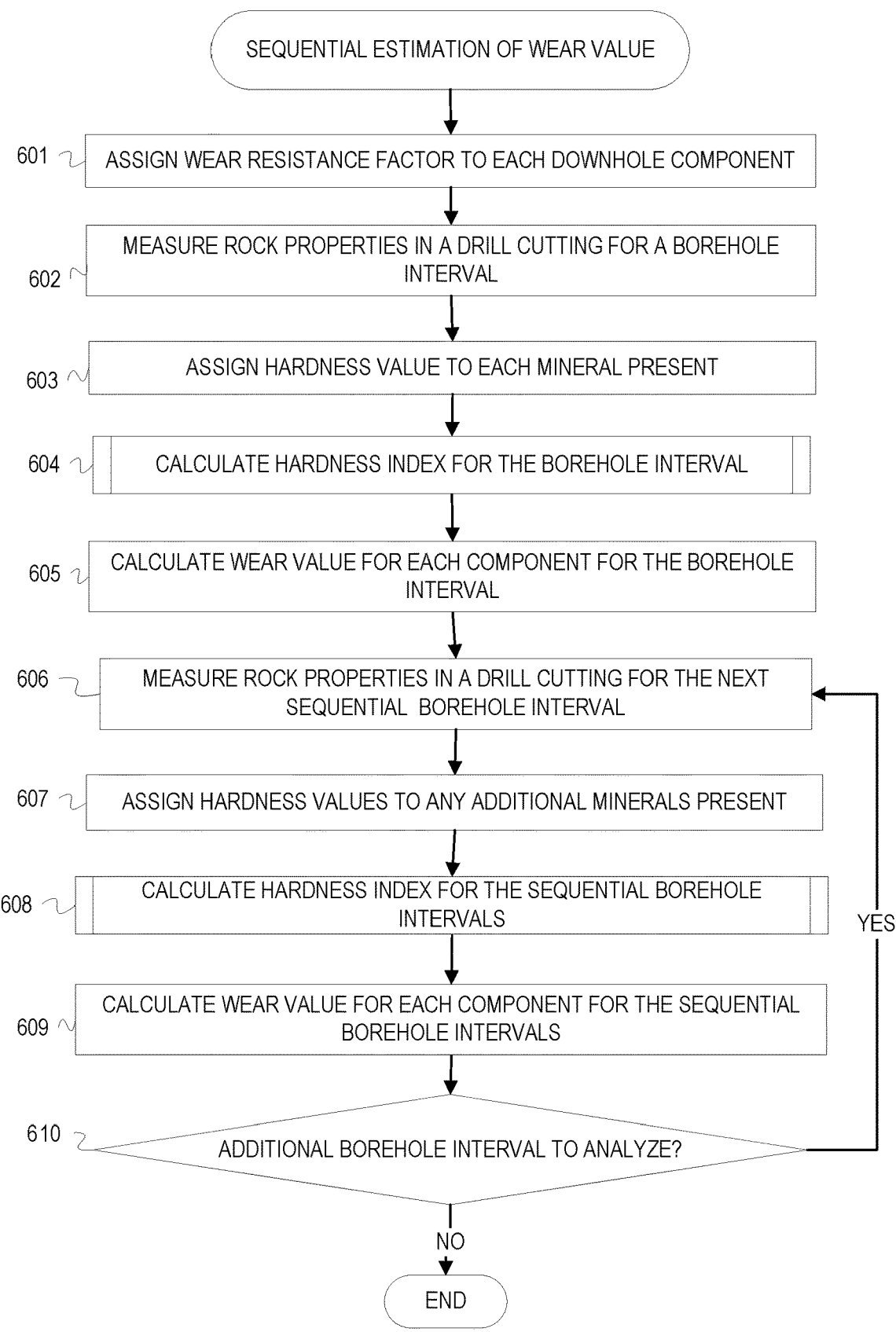
FIG. 6 depicts a flowchart of operations for sequentially estimating wear value.

FIG. 4-6 depict example operations for additional calculations and application of a hardness value and wear life value. Some operations overlap with operations previously described in FIGS. 2 and 3. Operations previously described in FIGS. 2 and 3 will not be described in detail again.

FIG. 4 depicts a flowchart of operations for an application of the wear value while drilling. Operations of FIG. 4 begin at block 401.

At block 401, a wear life estimator assigns a wear resistance factor to each downhole component, as in block 201 of FIG. 2.

At block 402, the wear life estimator determines a wear threshold range for each BHA component. The wear threshold range for each BHA component defines a range of values in which continued drilling operations may begin to compromise the integrity of the BHA component. The wear threshold range may be defined as a numerical value in terms of millimeters of wear on a material or as a percent wear value.

At block 403, rock properties of a drill cutting are measured, as in block 202 of FIG. 2.

At block 404, the wear life estimator assigns a hardness value to each mineral detected from the sample analysis or downhole measurements, as in block 203 of FIG. 2.

At block 405, a hardness index calculator calculates a hardness index for a drilled borehole interval, as in block 204 of FIG. 2 which is described in further detail in FIG. 3.

At block 406, the wear life evaluator determines the wear value for each BHA component, as in block 205 of FIG. 2.

At block 407, the wear life estimator determines if the wear value for any BHA component is within the threshold range for that component determined in block 402. If none of the BHA components are within the determined threshold range, drilling continues for a new borehole interval, and operations return to block 403. If any of the BHA components are within the wear threshold range, the drill string is pulled out of the borehole.

FIG. 5 depicts a flowchart of operations for designing a BHA based on borehole hardness. Operations of FIG. 5 begin at block 501.

At block 501, a wear life estimator estimates the rock properties in a predicted borehole. After determining a desired borehole location, well log data from nearby wells and/or geological formation surveys are analyzed to estimate or predict the rock properties in the desired borehole location. Similar to block 202 of FIG. 2, estimated rock properties comprise estimates of the mineralogy of the borehole such as the elemental composition and mineral type and concentration present in desired borehole location, as determined by current data.

At block 502, the wear life estimator assigns a value to each mineral predicted to be in the borehole, similar to block 203 of FIG. 2.

At block 503, a hardness index calculator calculates the hardness index for the borehole, similar to block 204 of FIG. 2 which is described in further detail in FIG. 3.

At block 504, the wear life estimator assigns a wear resistance factor to each BHA component, as in block 201 of FIG. 2.

At block 505, the wear life estimator determines wear resistance values for each BHA component that would allow the BHA to drill the borehole. Wear resistance values are determined in a similar manner as described in block 205 of FIG. 2. However, instead of determining the wear that has already occurred on a BHA component due to drilling, the wear life estimator predicts how much wear would occur on each BHA component throughout the process of drilling the borehole.

At block 506, a BHA is constructed based on the wear resistance values. The BHA is constructed by selecting various design parameters so that the wear resistance factor of each BHA component meets or exceeds the determined wear value for that component. This may be done by selecting materials, adding coatings, or incorporating other design aspects to enhance the wear factor of the BHA components.

FIG. 6 depicts a flowchart of operations for sequentially estimating wear value. While FIG. 2 depicts determining the cumulative borehole hardness value and cumulative wear value after each borehole interval has been analyzed, the cumulative values may also be determined sequentially as additional borehole intervals are drilled, as described in FIG. 6. Operations of FIG. 6 begin at block 601.

At block 601, a wear life estimator assigns a wear resistance factor to each downhole component, as in block 201 of FIG. 2.

At block 602, rock properties of a drill cutting corresponding to a first borehole interval are measured, as in block 202 of FIG. 2.

At block 603, the wear life estimator assigns a value to each mineral present in the borehole interval, as in block 203 of FIG. 2.

At block 604, a hardness index calculator calculates the hardness index for the borehole interval, similar to block 204 of FIG. 2 which is described in further detail in FIG. 3.

At block 605, the wear life estimator calculates a wear value for each BHA component for the borehole interval, as in block 205 of FIG. 2.

At block 606, rock properties in a drill cutting for the next sequential borehole interval are measured, as in block 602.

At block 607, the wear life estimator assigns hardness values to any additional minerals present in the current borehole interval. The assignment of hardness values for the minerals in the current borehole interval is consistent with any previously assigned hardness values. Minerals present in both drill cuttings have the same hardness value.

At block 608, a hardness index calculator calculates a hardness index for the sequential borehole intervals. The process for calculating the hardness index is similar to the operations of FIG. 3, however, the hardness index is calculated for both sequential borehole intervals at the same time.

At block 609, the wear life estimator calculates a wear value for each component over the sequential borehole intervals based on the hardness index of the sequential borehole intervals. Operations of block 609 are substantially similar to block 605.

At block 610 the wear life estimator determines if there are additional borehole intervals to analyze. If so, operations return to block 606 where any sequential borehole interval values are incorporated into the previously calculated values. If no borehole intervals remain unanalyzed, operations end. This process may be iterative and continue until a desired depth is reached or until the entire borehole has been analyzed. This method of determining the cumulative hardness value and wear value may allow the wear value to be calculated dynamically or manually at various times throughout the drilling process.

Variations

While FIGS. 1, 2, and 3 depict example embodiments of methods for and applications of estimating wear on BHA components and determining a hardness index for a borehole, variations upon these methods may be applied without changing the scope of the technology. For example, calculating the wear value as in block 205 of FIG. 2 may be based on expected wellbore rock properties of the formation to be drilled. This allows the prediction on when the BHA should be pulled out of hole to be updated while drilling. A flag recommending the BHA be pulled out of hole can be provided based on the wear life estimate of block 209. The flag may be calculated downhole. Furthermore, the rock properties, as measured in block 201, may be measured by a downhole BHA component. The rock properties may also be measured on the surface by XRD analysis of drilled cuttings.

Example Systems

Figure 7:
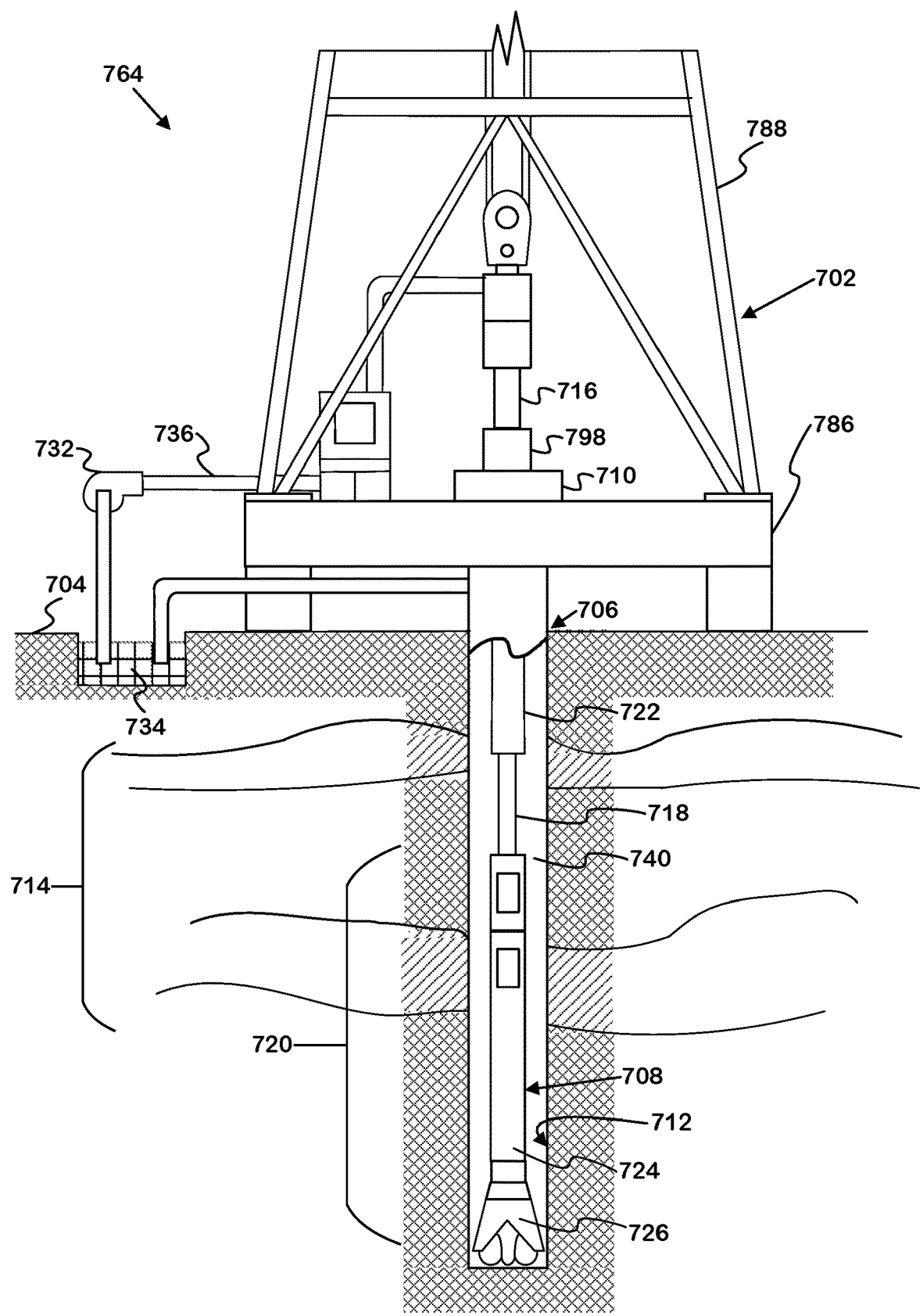
FIG. 7 is a schematic diagram of a drilling rig system, according to some embodiments.

FIG. 7 is a schematic diagram of a drilling rig system, according to some embodiments. For example, in FIG. 7 it can be seen how a system 764 may also form a portion of a drilling rig 702 located at the surface 704 of a well 706. Drilling of oil and gas wells is commonly carried out using a string of drill pipes connected together so as to form a drilling string 708 that is lowered through a rotary table 710 into a wellbore or borehole 712. Here a drilling platform 786 is equipped with a derrick 788 that supports a hoist.

The drilling rig 702 may thus provide support for the drill string 708. The drill string 708 may operate to penetrate the rotary table 710 for drilling the borehole 712 through subsurface formations 714. The drill string 708 includes a Kelly 716, drill pipe 718, and a bottom hole assembly (BHA) 720 located at the lower portion of the drill pipe 718.

The BHA 720 includes drill collars 722, a down hole tool 724, and a drill bit 726. The drill bit 726 may operate to create a borehole 712 by penetrating the surface 704 and subsurface formations 714. The down hole tool 724 may comprise any of a number of different types of tools including MWD tools, LWD tools, and others.

During drilling operations, the drill string 708 (including the Kelly 716, the drill pipe 718, and the BHA 720) may be rotated by the rotary table 710. In addition to, or alternatively, the BHA 720 may also be rotated by a motor (e.g., a mud motor) that is located down hole. The drill collars 722 may be used to add weight to the drill bit 726. The drill collars 722 may also operate to stiffen the BHA 720, allowing the BHA 720 to transfer the added weight to the drill bit 726, and in turn, to assist the drill bit 726 in penetrating the surface 704 and subsurface formations 714.

During drilling operations, a mud pump 732 may pump drilling fluid (sometimes known by those of ordinary skill in the art as "drilling mud") from a mud pit 734 through a hose 736 into the drill pipe 718 and down to the drill bit 726. The drilling fluid can flow out from the drill bit 726 and be returned to the surface 704 through an annular area 740 between the drill pipe 718 and the sides of the borehole 712. The drilling fluid may then be returned to the mud pit 734, where such fluid is filtered. In some embodiments, the drilling fluid can be used to cool the drill bit 726, as well as to provide lubrication for the drill bit 726 during drilling operations. Additionally, the drilling fluid may be used to remove subsurface formation 714 cuttings created by operating the drill bit 726.

Figure 8:
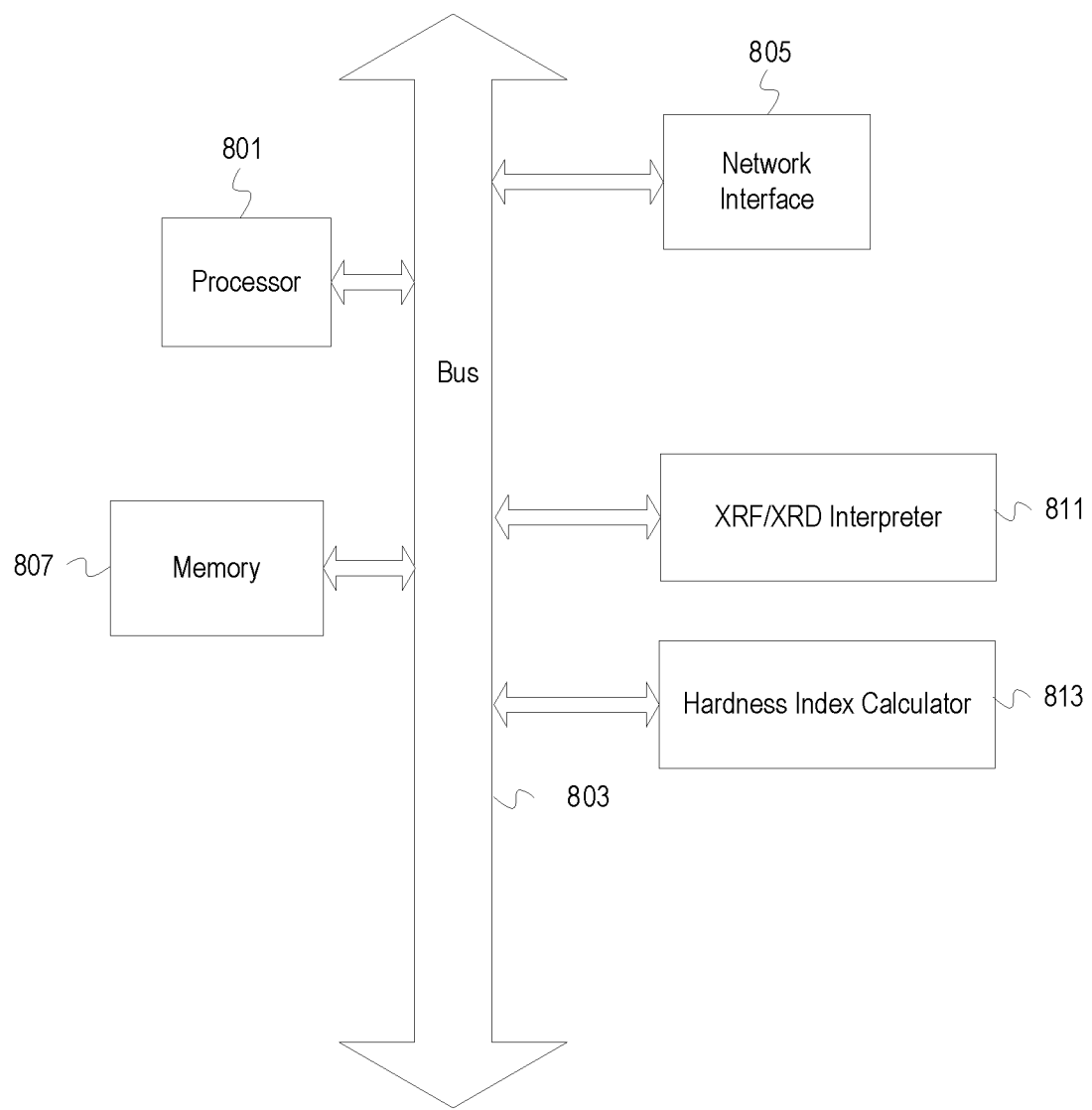
FIG. 8 depicts an example computer, according to some embodiments.

FIG. 8 depicts an example computer, according to some embodiments. The computer includes a processor 801 (possibly including multiple processors, multiple cores, multiple nodes, and/or implementing multi-threading, etc.). The computer includes memory 807. The memory 807 may be system memory or any one or more of the above already described possible realizations of machine-readable media. The system also includes a bus 803 and a network interface 805.

The system also includes an XRF/XRD interpreter 811 and a hardness index calculator 813. The XRF/XRD interpreter 811 can perform operations of interpreting XRF and XRD data from spectral lines into elemental composition and physical characteristics of the rock sample, as described above. The hardness index calculator 813 incorporates the interpreted XRF and XRD data with properties of the borehole and drilling parameters to determine a hardness for the drilled borehole interval. Any one of the previously described functionalities may be partially (or entirely) implemented in hardware and/or on the processor 801. For example, the functionality may be implemented with an application specific integrated circuit, in logic implemented in the processor 801, in a co-processor on a peripheral device or card, etc. Further, realizations may include fewer or additional components not illustrated in FIG. 8 (e.g., video cards, audio cards, additional network interfaces, peripheral devices, etc.). The processor 801 and the network interface 805 are coupled to the bus 803. Although illustrated as being coupled to the bus 803, the memory 807 may be coupled to the processor 801.

The flowcharts are provided to aid in understanding the illustrations and are not to be used to limit scope of the claims. The flowcharts depict example operations that can vary within the scope of the claims. Additional operations may be performed; fewer operations may be performed; the operations may be performed in parallel; and the operations may be performed in a different order. It will be understood that each block of the flowchart illustrations and/or block diagrams, and combinations of blocks in the flowchart illustrations and/or block diagrams, can be implemented by program code. The program code may be provided to a processor of a general-purpose computer, special purpose computer, or other programmable machine or apparatus.

As will be appreciated, aspects of the disclosure may be embodied as a system, method, or program code/instructions stored in one or more machine-readable media. Accordingly, aspects may take the form of hardware, software (including firmware, resident software, micro-code, etc.), or a combination of software and hardware aspects that may all generally be referred to herein as a "circuit," "module" or "system." The functionality presented as individual modules/units in the example illustrations can be organized differently in accordance with any one of platform (operating system and/or hardware), application ecosystem, interfaces, programmer preferences, programming language, administrator preferences, etc.

Any combination of one or more machine-readable medium(s) may be utilized. The machine-readable medium may be a machine-readable signal medium or a machine-readable storage medium. A machine-readable storage medium may be, for example, but not limited to, a system, apparatus, or device, that employs any one of or combination of electronic, magnetic, optical, electromagnetic, infrared, or semiconductor technology to store program code. More specific examples (a non-exhaustive list) of the machine-readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a machine-readable storage medium may be any tangible medium that can contain or store a program for use by or in connection with an instruction execution system, apparatus, or device. A machine-readable storage medium is not a machine-readable signal medium.

A machine-readable signal medium may include a propagated data signal with machine-readable program code embodied therein, for example, in baseband or as part of a carrier wave. Such a propagated signal may take any of a variety of forms, including, but not limited to, electromagnetic, optical, or any suitable combination thereof. A machine-readable signal medium may be any machine-readable medium that is not a machine-readable storage medium and that can communicate, propagate, or transport a program for use by or in connection with an instruction execution system, apparatus, or device.

Program code embodied on a machine-readable medium may be transmitted using any appropriate medium, including but not limited to wireless, wireline, optical fiber cable, RF, etc., or any suitable combination of the foregoing.

Computer program code for carrying out operations for aspects of the disclosure may be written in any combination of one or more programming languages, including an object oriented programming language such as the Java® programming language, C++ or the like; a dynamic programming language such as Python; a scripting language such as Perl programming language or PowerShell script language; and conventional procedural programming languages, such as the "C" programming language or similar programming languages. The program code may execute entirely on a stand-alone machine, may execute in a distributed manner across multiple machines, and may execute on one machine while providing results and or accepting input on another machine.

The program code/instructions may also be stored in a machine-readable medium that can direct a machine to function in a particular manner, such that the instructions stored in the machine-readable medium produce an article of manufacture including instructions which implement the function/act specified in the flowchart and/or block diagram block or blocks.

While the aspects of the disclosure are described with reference to various implementations and exploitations, it will be understood that these aspects are illustrative and that the scope of the claims is not limited to them. In general, techniques for estimating wear on BHA components utilizing a rock hardness index as described herein may be implemented with facilities consistent with any hardware system or hardware systems. Many variations, modifications, additions, and improvements are possible.

Plural instances may be provided for components, operations, or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the disclosure. In general, structures and functionality presented as separate components in the example configurations may be implemented as a combined structure or component. Similarly, structures and functionality presented as a single component may be implemented as separate components. These and other variations, modifications, additions, and improvements may fall within the scope of the disclosure.

Use of the phrase "at least one of" preceding a list with the conjunction "and" should not be treated as an exclusive list and should not be construed as a list of categories with one item from each category, unless specifically stated otherwise. A clause that recites "at least one of A, B, and C" can be infringed with only one of the listed items, multiple of the listed items, and one or more of the items in the list and another item not listed.

Example Embodiments

A method comprises determining a mineral composition of a borehole interval from at least one of drilled cuttings and borehole data, determining a hardness value for each mineral identified in the determined mineral composition, and calculating a hardness value for the borehole interval. The hardness value for the borehole interval is based on a proportion of each mineral identified in the determined mineral composition.

The method further comprises determining a mineral composition of each of two or more borehole intervals from at least one of drilled cuttings and borehole data for each of two or more borehole intervals, determining a hardness value for each mineral identified in the determined mineral composition for each of the two or more borehole intervals, and calculating a hardness value for each of the two or more borehole intervals, wherein the hardness value for each of the two or more borehole intervals is based on the proportion of each mineral identified in the determined mineral composition for each of the two or more borehole intervals. Like minerals between the two or more borehole intervals have the same hardness value The method further comprises calculating a hardness value for the borehole based on the hardness values for each of the two or more borehole intervals. The hardness value for the borehole is a sum of the hardness values for each of the two or more borehole intervals. Determining a hardness value for each mineral identified in the determined mineral composition comprises assigning a relative hardness value to each mineral based on a comparative hardness of the identified minerals.

Calculating a hardness value for the borehole interval comprises identifying a percent composition of each mineral in the determined mineral composition, multiplying the percent composition of each mineral by the hardness value for the mineral to obtain a relative hardness composition value for each mineral identified, and summing the relative hardness composition values for each mineral to obtain the hardness value for the borehole interval.

Determining the mineral composition of a borehole interval further comprises measuring rock properties of the minerals by X-ray diffraction (XRD) on the drilled cuttings. The borehole interval is a predetermined length based on the borehole length or a predetermined time based on drilling time. The borehole interval is determined based on an expected wear value for components of a bottom hole assembly.

A system comprises a processor and a machine-readable medium having program code executable by the processor to cause the system to determine a mineral composition of a borehole interval from at least one of drilled cuttings and borehole data, determine a hardness value for each mineral identified in the determined mineral composition, and calculate a hardness value for the borehole interval. The hardness value for the borehole interval is based on the proportion of each mineral identified in the determined mineral composition.

The system further comprises a machine-readable medium having program code executable by the processor to cause the system to determine a mineral composition of each of two or more borehole intervals from at least one of drilled cuttings and borehole data for each of the two or more borehole intervals, determine a hardness value for each mineral identified in the determined mineral composition for each of the two or more borehole intervals, and calculate a hardness value for each of the two or more borehole intervals, wherein the hardness values for the borehole intervals are based on the proportion of each mineral identified in the determined mineral composition. Like minerals between the two or more borehole intervals have the same hardness value.

The system further comprises the machine-readable medium having program code executable by the processor to cause the system to calculate a hardness value for the borehole based on the hardness value for the two or more borehole intervals.

The program code to determine a hardness value for each mineral identified in the determined mineral composition comprises program code executable by the processor to cause the system to assign a relative hardness value to each mineral based on the comparative hardness of the identified minerals.

The program code to assign a relative hardness value to each mineral based on the comparative hardness of the identified minerals comprises program code executable by the processor to assign a value of 1 to the softest identified mineral, assign a value of 9 to the hardest identified mineral, and assign a value between 1 and 9 to each remaining identified mineral based on a comparative hardness.

The program code to calculate a hardness value for the borehole interval further comprises program code executable by the processor to cause the system to identify the percent composition of each mineral in the determined mineral composition, multiply the percent composition of each mineral by the hardness value for the mineral to obtain a relative hardness composition value for each mineral identified, and sum the relative hardness composition values for each mineral to obtain the hardness value for the borehole interval.

The borehole interval is a predetermined length based on the borehole length, a predetermined time, or the borehole interval is determined based on an expected wear value for components of a bottom hole assembly.

A method comprises determining a hardness value for each mineral identified from at least one of drilled cuttings and borehole data, calculating a hardness index for a drilled borehole interval based, at least in part, on the hardness values, and calculating a wear value for each component of a bottom hole assembly (BHA) based on the hardness index for the drilled borehole interval, wear resistance values of each of the BHA components, and a drilling parameter.

The method further comprises indicating the calculated wear values for a BHA design.

The method further comprises estimating when the BHA should be pulled out of a borehole based on the calculated wear values of the BHA components.

The method further comprises identifying the minerals present in drilled cuttings or identifying the minerals from borehole data.

The method further comprising measuring rock properties of the minerals by X-ray diffraction (XRD) on the drilled cuttings.

What is claimed is:

1. A method comprising:
   determining a mineral composition of a borehole interval of a borehole from at least one of drilled cuttings and borehole data;
   determining a hardness value for each mineral identified in the determined mineral composition of the borehole interval; and
   calculating a hardness value for the borehole interval, wherein the hardness value for the borehole interval is based on a proportion of each mineral identified in the determined mineral composition of the borehole interval.

2. The method of claim 1, further comprising:
   determining a mineral composition of each of two or more borehole intervals from at least one of drilled cuttings and borehole data for each of the two or more borehole intervals;
   determining a hardness value for each mineral identified in the determined mineral composition for each of the two or more borehole intervals, wherein like minerals between the two or more borehole intervals have a same hardness value; and
   calculating a hardness value for each of the two or more borehole intervals, wherein the hardness value for each of the two or more borehole intervals is based on a proportion of each mineral identified in the determined mineral composition for each of the two or more borehole intervals.

3. The method of claim 2, further comprising:
   calculating a hardness value for the borehole based on the hardness value for each of the two or more borehole intervals, wherein the hardness value for the borehole is a sum of hardness values of the two or more borehole intervals.

4. The method of claim 1, wherein determining the hardness value for each mineral identified in the determined mineral composition of the borehole interval comprises assigning a relative hardness value to each mineral identified in the determined mineral composition based on a comparative hardness of each mineral identified in the determined composition.

5. The method of claim 1, wherein calculating the hardness value for the borehole interval comprises:
   identifying a percent composition of each mineral identified in the determined mineral composition;
   multiplying the percent composition of each mineral identified in the determined mineral composition by the hardness value for each mineral identified in the determined mineral composition to obtain a relative hardness composition value for each mineral identified in the determined mineral composition; and
   summing the relative hardness composition value for each mineral identified in the determined mineral composition to calculate the hardness value for the borehole interval.

6. The method of claim 1, wherein determining the mineral composition of the borehole interval comprises measuring rock properties of each mineral identified in the determined mineral composition by X-ray diffraction (XRD) on the drilled cuttings.

7. The method of claim 1, wherein the borehole interval indicates a length of the borehole or a drilling time in the borehole.

8. The method of claim 1, wherein the borehole interval is determined based on an expected wear value for components of a bottom hole assembly used to drill the borehole.

9. A system comprising:
   a processor; and
   a machine-readable medium having program code executable by the processor to cause the system to:
   determine a mineral composition of a borehole interval of a borehole from at least one of drilled cuttings and borehole data,
   determine a hardness value for each mineral identified in the determined mineral composition of the borehole interval, and
   calculate a hardness value for the borehole interval, wherein the hardness value for the borehole interval is based on a proportion of each mineral identified in the determined mineral composition of the borehole interval.

10. The system of claim 9, wherein the machine-readable medium having program code executable by the processor to cause the system to:
    determine a mineral composition of each of two or more borehole intervals from at least one of drilled cuttings and borehole data for each of the two or more borehole intervals;
    determine a hardness value for each mineral identified in the determined mineral composition for each of the two or more borehole intervals, wherein like minerals between the two or more borehole intervals have a same hardness value; and calculate a hardness value for each of the two or more borehole intervals, wherein the hardness value for each of the two or more borehole intervals is based on a proportion of each mineral identified in the determined mineral composition for each of the two or more borehole intervals.

11. The system of claim 10, wherein the program code is further executable by the processor to cause the system to calculate a hardness value for the borehole based on the hardness value for each of the two or more borehole intervals.

12. The system of claim 9, wherein the program code executable by the processor to determine the hardness value for each mineral identified in the determined mineral composition of the borehole interval further comprises program code executable by the processor to cause the system to assign a relative hardness value to each mineral based on a comparative hardness of each mineral identified in the determined composition.

13. The system of claim 12, wherein the program code executable by the processor to assign the relative hardness value to each mineral based on the comparative hardness of each mineral identified in the determined composition is configured to further cause the processor to:

assign a value of 1 to a softest identified mineral;
assign a value of 9 to a hardest identified mineral; and
assign a value between 1 and 9 to each remaining identified mineral based on the comparative hardness of each mineral identified in the determined composition.

14. The system of claim 9, wherein the program code executable by the processor to calculate the hardness value for the borehole interval is configured to further cause the system to:

identify a percent composition of each mineral identified in the determined mineral composition;
multiply the percent composition of each mineral identified in the determined mineral composition by the hardness value for each mineral identified in the determined mineral composition to obtain a relative hardness composition value for each mineral identified in the determined mineral composition; and
calculate the hardness value for the borehole interval by adding together each relative hardness composition value.

15. The system of claim 9, wherein the borehole interval indicates a length of the borehole, a predetermined drilling time in the borehole, or the borehole interval is determined based on an expected wear value for components of a bottom hole assembly.

16. A method comprising:

determining a hardness value for each mineral identified from at least one of drilled cuttings and borehole data;
calculating a hardness index for a drilled borehole interval based, at least in part, on the hardness value of each mineral identified; and
calculating a wear value for each component of a plurality of components of a bottom hole assembly (BHA) based on the hardness index for the drilled borehole interval, a wear resistance value of each component of the plurality of components of the BHA, and a drilling parameter.

17. The method of claim 16, further comprising:

indicating the calculated wear value for each component of a BHA design.

18. The method of claim 16, further comprising:

estimating when the BHA should be pulled out of a borehole based on the calculated wear value for each component of the plurality of components of the BHA.

19. The method of claim 16, further comprising:

identifying each mineral present in the drilled cuttings in the borehole data.

20. The method of claim 16, further comprising:

measuring rock properties of each mineral identified by X-ray diffraction (XRD) on the drilled cuttings.

* * * * *